United States Patent
Bodhuri et al.

(10) Patent No.: US 8,101,609 B2
(45) Date of Patent: Jan. 24, 2012

(54) PROCESSES FOR THE PREPARATION OF RIVAROXABAN AND INTERMEDIATES THEREOF

(75) Inventors: Prabhudas Bodhuri, Brantford (CA); Gamini Weeratunga, Ancaster (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 12/767,436

(22) Filed: Apr. 26, 2010

(65) Prior Publication Data

US 2010/0273790 A1  Oct. 28, 2010

Related U.S. Application Data

(62) Division of application No. 12/431,272, filed on Apr. 28, 2009, now Pat. No. 7,816,355.

(51) Int. Cl.
- *A61K 31/5377* (2006.01)
- *C07D 413/14* (2006.01)
- *C07D 413/10* (2006.01)
- *C07D 295/155* (2006.01)

(52) U.S. Cl. .................. 514/236.8; 544/137; 544/147; 544/166

(58) Field of Classification Search .......... 514/230.8; 544/166, 147, 137
See application file for complete search history.

(56) References Cited

U.S. PATENT DOCUMENTS

| | | | |
|---|---|---|---|
| 7,157,456 B2 | 1/2007 | Straub et al. | |
| 7,351,823 B2 | 4/2008 | Berwe et al. | |
| 2007/0026065 A1 | 2/2007 | Benke et al. | |
| 2007/0066611 A1 | 3/2007 | Thomas et al. | |
| 2007/0149522 A1 | 6/2007 | Thomas | |
| 2008/0026057 A1 | 1/2008 | Benke | |
| 2009/0004265 A1 | 1/2009 | Misselwitz et al. | |

FOREIGN PATENT DOCUMENTS

| | | |
|---|---|---|
| CA | 2624310 | 9/2006 |
| CA | 2624306 | 4/2007 |
| CA | 2624963 | 4/2007 |
| CA | 2642376 | 8/2007 |
| WO | 01/47919 | 7/2001 |
| WO | 2004/060887 | 7/2004 |
| WO | 2008/022786 | 2/2008 |
| WO | 2008/128653 | 10/2008 |

OTHER PUBLICATIONS

Mederski et al., A General Synthesis of 1-Aryl Carbamoyl-2-alkyl-4-aryl Substituted Semicarbazides as Nonbasic Factor Xa Inhibitors, 2003, Bioorganic & Medicinal Chemistry Letters, 13, 3715-3718.*
U.S. Appl. No. 12/208,703.
DWPI Abstract of WO-2008/022786, 2008.
DWPI Abstract of WO-2008/128653, 2008.
Escolar, G. et al.; Rivaroxaban: factor Xa inhibitor anticoagulant; Drugs of the future; 2006; p. 484-493, 31(6).
Kakar, P. et al.; Drug Evaluation: rivaroxaban, an oral, direct inhibitor of activacted Factor X; 2007, p. 256-265, 8(3).
Roehrig, S. et al.; Discovery of the novel antithrombotic agent . . . J. of Medicinal Chemistry, 2005; p. 5900-5908, 48(19)/.
Rohde, G.; Determination of rivaroxaban—a novel, oral, direct Factor Xa inhibitor . . . Anal.Tech. in the Biomed and Life Science; 2008;v p. 43-50; (872(1-2).

* cited by examiner

*Primary Examiner* — Kamal Saeed
*Assistant Examiner* — Kristin Bianchi

(57) ABSTRACT

This invention provides a process for the preparation of S-Rivaroxaban and/or R-Rivaroxaban comprising reacting, in the presence of a first base, a compound of Formula 9:

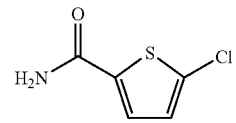

9 with a compound of Formula 8:

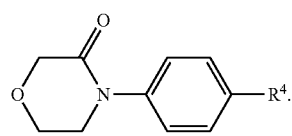

8

22 Claims, No Drawings

PROCESSES FOR THE PREPARATION OF RIVAROXABAN AND INTERMEDIATES THEREOF

This is a Division of U.S. application Ser. No. 12/431,272 filed on Apr. 28, 2009.

TECHNICAL FIELD

The present invention relates to the field of chemical synthesis of organic compounds and in particular to methods for the synthesis of Rivaroxaban and intermediates thereof.

BACKGROUND

Rivaroxaban (1) (5-chloro-N-{[(5S)-2-oxo-3-[4-(3-oxo-morpholin-4-yl)phenyl]oxazolidin-5-yl]methyl}thiophene-2-carboxamide) is a low molecular weight, orally administrable anticoagulant drug. The pharmaceutical directly inhibits the active form of serine protease Factor Xa (FXa). Rivaroxaban can be used for the prevention and treatment of various thromboembolic diseases, in particular of deep vein thrombosis (DVT), pulmonary embolism (PE), myocardial infract, angina pectoris, reocclusions and restenoses after angioplasty or aortocoronary bypass, cerebral stroke, transitory ischemic attacks, and peripheral arterial occlusive diseases.

Rivaroxaban is disclosed in WO 01/47919 and has the following structure:

(1)

US2007/0149522 relates to a method for producing 5-chloro-N-({5S)-2-oxo-3-[4-(3-oxo-4-morpholinyl)-phenyl]-1,3-oxazolidin-5-yl}-methyl)-2-thiophene carboxamide starting from 5-chlorothiophene-2-carbonyl chloride and (2S)-3-amino-propane-1,2-diol and 4-(4-aminophenyl)-3-morpholinone.

US2007/0066611 relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

U.S. Pat. No. 7,351,823 relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide starting from 2-[(2S)-2-oxiranylmethyl]-1H-isoindole-1,3-(2H)-dione, 4-(4-aminophenyl)-3-morpholinone and 5-chlorothiophene-2-carbonyl chloride.

WO 2009/023233 relates to novel compounds that are substituted oxazolidinones derivatives and pharmaceutically acceptable salts thereof. More specifically, this invention relates to novel oxazolidinone compounds that are derivatives of Rivaroxaban. The invention also provides pyrogen-free compositions comprising one or more compounds of the invention and a carrier, along with the use of the disclosed compounds and compositions in methods of treating diseases and condition that are beneficially treated by administering a selective inhibitor of factor Xa, such as Rivaroxaban.

SUMMARY

This invention is based, in part, on preparing Rivaroxaban by reacting a compound of Formula 8a, 8b or 8c with 5-chlorothiophene-2-carboxamide of Formula 9 in Scheme 1.

The present invention is directed to methods of preparation of Rivaroxaban, various intermediates useful in the preparation of Rivaroxaban and methods of preparation of such intermediates.

In illustrative embodiments of the present invention, Rivaroxaban and the intermediates thereof may be prepared by an exemplary process as set out in Scheme 1. Exemplary reagents and conditions for these reactions are disclosed herein.

Scheme 1

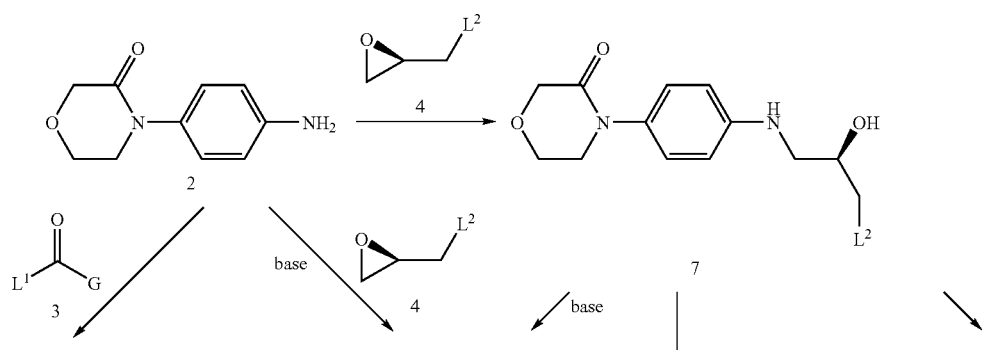

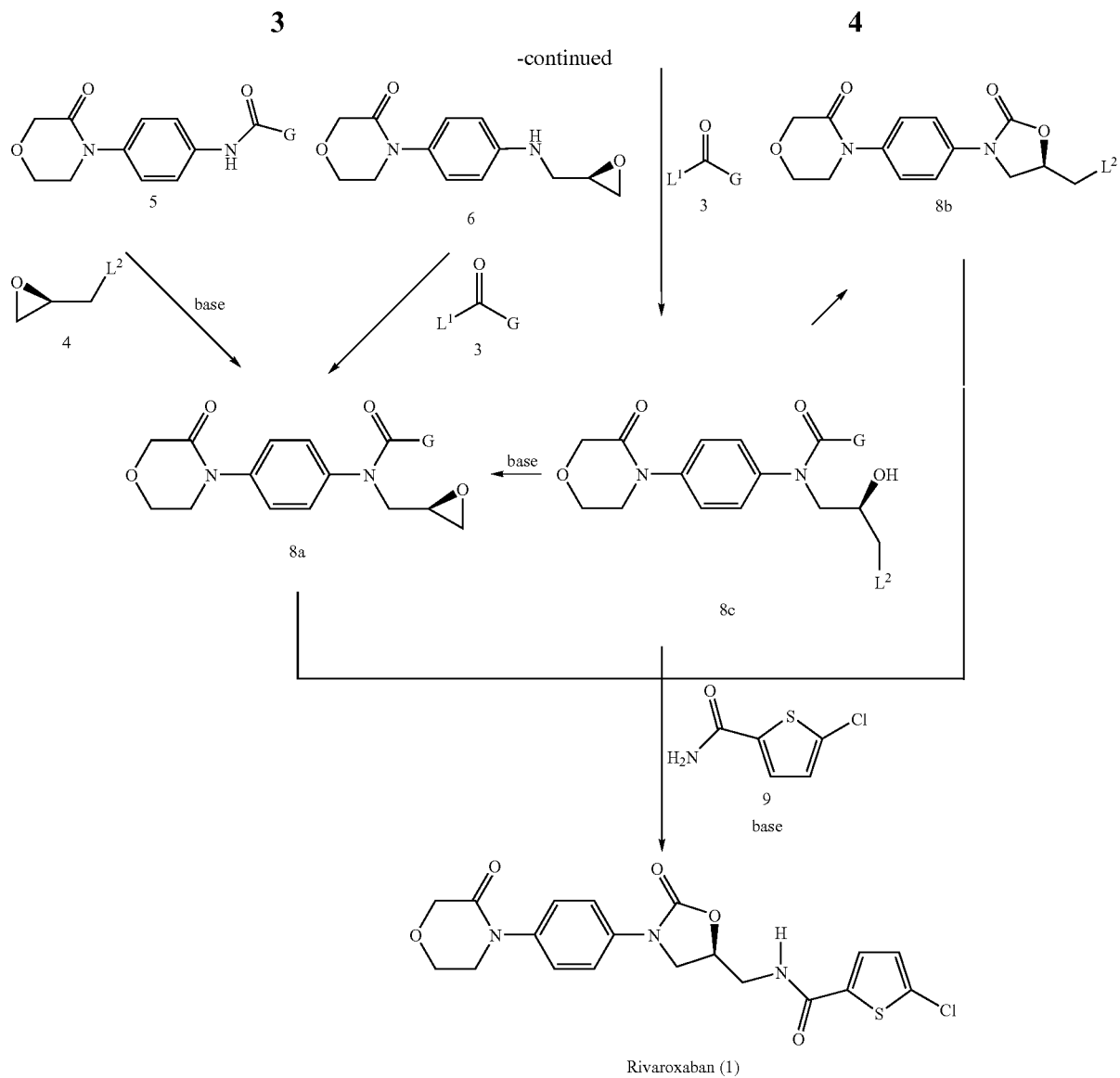
In illustrative embodiments of the present invention, the (R)-enantiomer of Rivaroxaban is prepared by the processes of the present invention by replacing the compound of Formula 4 of Scheme 1 with the (S)-enantiomer (ie. (S)-(+)-epichlorohydrin) and preparing compounds having the stereochemistry as shown in Scheme 1a.
Scheme 1a
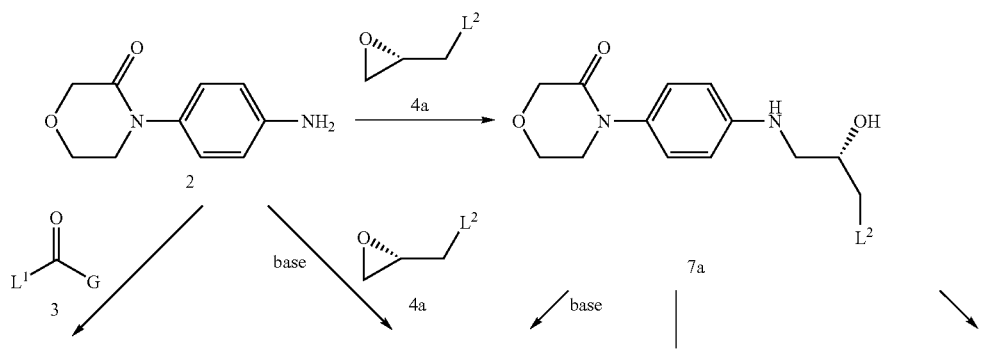

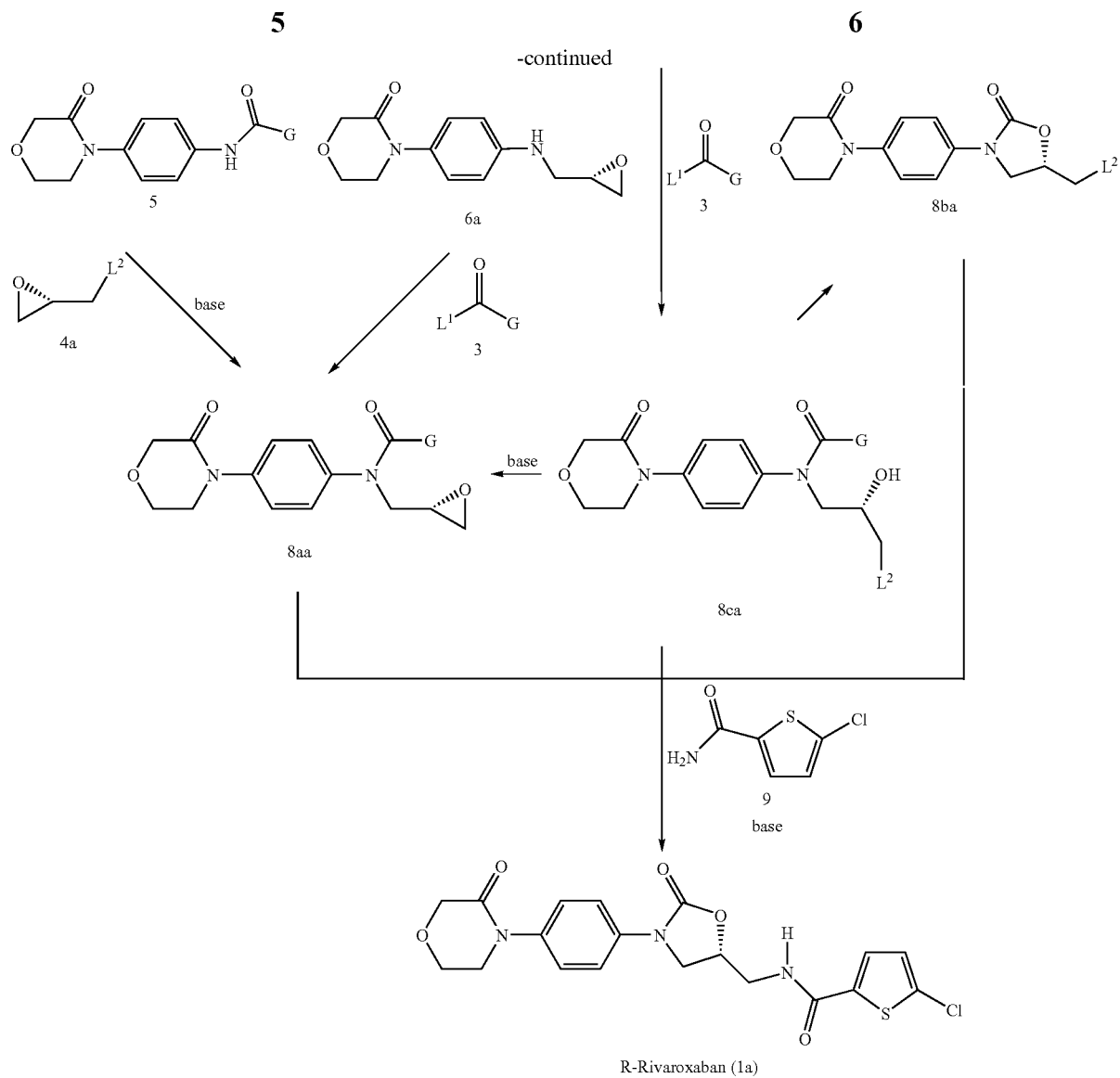
-continued
R-Rivaroxaban (1a)
In illustrative embodiments of the present invention, there is provided a process for the preparation of S-Rivaroxaban and/or R-Rivaroxaban comprising reacting, in the presence of a first base, a compound of Formula 9:
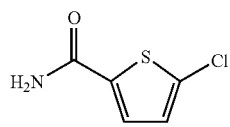
with a compound of Formula 8:
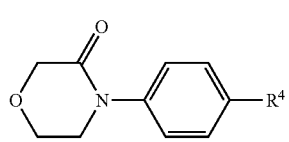
wherein $R^4$ is selected from the group consisting of:
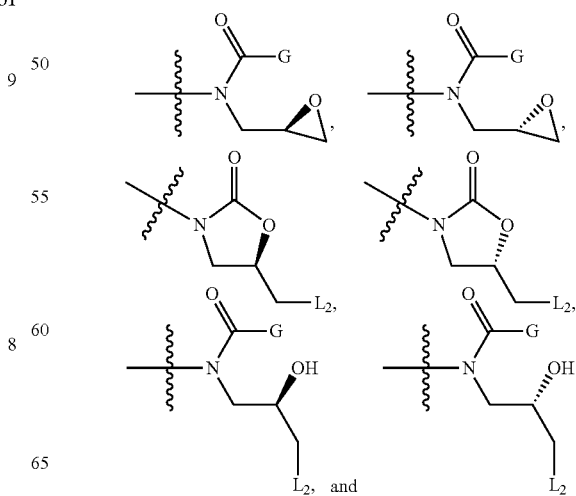

wherein
G is OR¹, NR²R³, or CX₃;
R¹ is alkyl, substituted alkyl, aryl, substituted aryl, arylalkyl, or substituted aryl alkyl;
R² and R³ are either (a) two independent groups or (b) together form a single ring group with the N to which they are bonded;
R² and R³, when independent groups, are independently selected from the group consisting of: H, alkyl, substituted alkyl, aryl, substituted aryl, arylalkyl and substituted arylalkyl;
R² and R³, when together form a single ring group with the N to which they are bonded, are a heteroaryl ring;
X is halogen; and
L² is a halogen or sulfonyloxy group.

In illustrative embodiments of the present invention, there is provided a process described herein wherein a compound of Formula 8 is a compound of Formula 8a and/or 8aa:

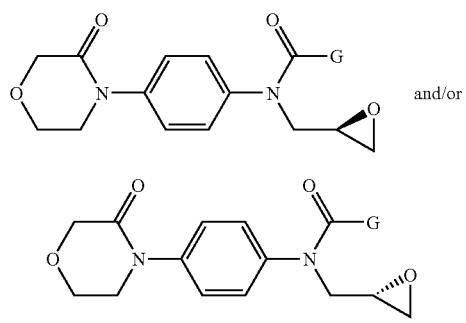

and/or

In illustrative embodiments of the present invention, there is provided a process described herein wherein a compound of Formula 8 is a compound of Formula 8b and/or 8ba:

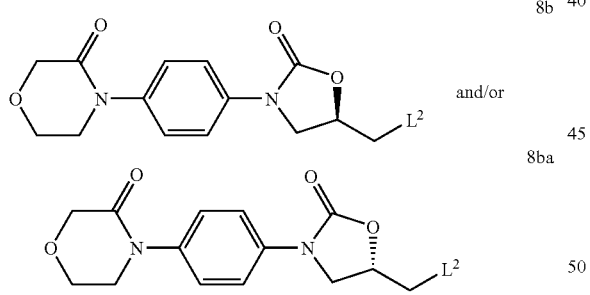

and/or

In illustrative embodiments of the present invention, there is provided a process described herein wherein a compound of Formula 8 is a compound of Formula 8c and/or 8ca:

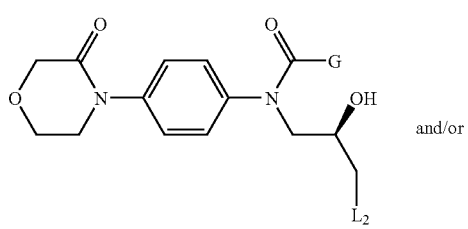

and/or

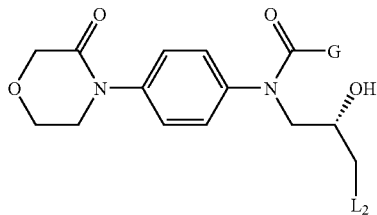

In illustrative embodiments of the present invention, there is provided a process for the preparation of a compound of Formula 8a:

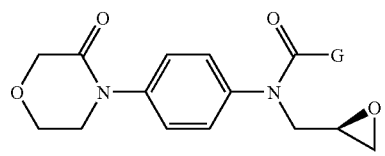

wherein
G is OR¹, NR²R³, or CX₃;
R¹ is alkyl, substituted alkyl, aryl, substituted aryl, arylalkyl, or substituted aryl alkyl;
R² and R³ are either (a) two independent groups or (b) together form a single ring group with the N to which they are bonded;
R² and R³, when independent groups, are independently selected from the group consisting of: H, alkyl, substituted alkyl, aryl, substituted aryl, arylalkyl and substituted arylalkyl;
R² and R³ when together form a single ring group with the N to which they are bonded, are a heteroaryl ring; and
X is halogen, the process comprising:
i. reacting, optionally in the presence of a second base, a compound of Formula 2:

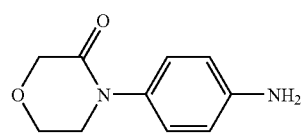

with a compound of Formula 3:

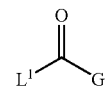

wherein
L¹ is a leaving group selected from the group consisting of halogen, imidazole, ester, C₁-C₄ alkoxy, trihalomethoxy, N-hydroxysuccinimide, p-nitrophenol, N-hydroxyphthalimide, and N-hydroxybenzotriazole; and
G is as defined above for Formula 8a, thereby forming a compound of Formula 5:

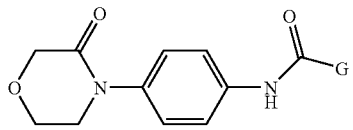

wherein G is as defined above for Formula 8a; and ii. reacting the compound of Formula 5, in the presence of a third base, with a compound of Formula 4:

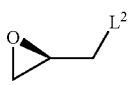

wherein $L^2$ is a halogen or sulfonyloxy group, thereby forming the compound of Formula 8a.

In illustrative embodiments of the present invention, there is provided a process for the preparation of a compound of Formula 8a:

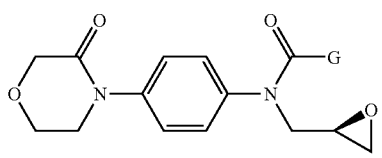

wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl;
$R^2$ and $R^3$ when together form a single ring group with the N to which they are bonded are a heteroaryl ring; and
X is halogen, the process comprising:
i. reacting, in the presence of a fourth base, a compound of Formula 2:

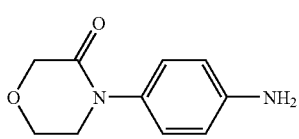

with a compound of Formula 4:

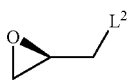

wherein $L^2$ is a halogen or sulfonyloxy group, thereby forming a compound of Formula 6:

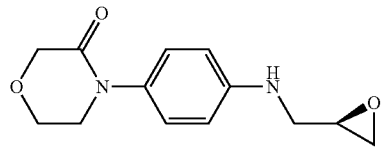

and;
ii. reacting, optionally in the presence of a fifth base, the compound of Formula 6 with a compound of Formula 3:

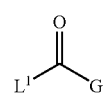

wherein
$L^1$ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and
G is as defined above for Formula 8a, thereby forming the compound of Formula 8a.

In illustrative embodiments of the present invention, there is provided a process for the preparation of a compound of Formula 8c:

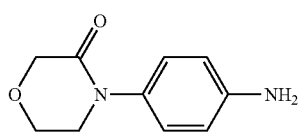

wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl;
$R^2$ and $R^3$ when together form a single ring group with the N to which they are bonded, are a heteroaryl ring; and
$L^2$ is a halogen or sulfonyloxy group, the process comprising:
i. reacting a compound of Formula 2:

with a compound of Formula 4:

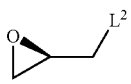
4 wherein L² is a halogen or sulfonyloxy group; thereby forming a compound of Formula 7:

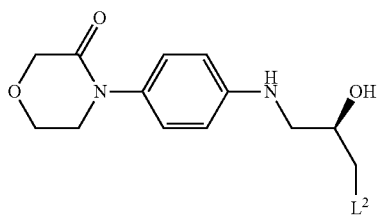
7 wherein
    L² is as defined for Formula 4; and
    ii. reacting, in the presence of a sixth base, the compound of Formula 7 with a compound of Formula 3:

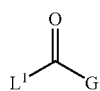
3 wherein
    L¹ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and
    G is as defined above for Formula 8c, thereby forming the compound of Formula 8c.

In illustrative embodiments of the present invention, there is provided a process for the preparation of a compound of Formula 8a:

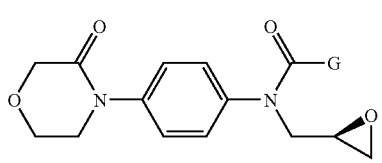
8a wherein
    G is $OR^1$, $NR^2R^3$, or $CX_3$;
    $R^1$ is alkyl, substituted alkyl, aryl, substituted aryl, arylalkyl, or substituted aryl alkyl;
    $R^2$ and $R^3$ are either (a) two independent groups or (b) together form a single ring group with the N to which they are bonded;
    $R^2$ and $R^3$, when independent groups, are independently selected from the group consisting of: H, alkyl, substituted alkyl, aryl, substituted aryl, arylalkyl and substituted arylalkyl;

$R^2$ and $R^3$, when together form a single ring group with the N to which they are bonded, are a heteroaryl ring;
    X is halogen,
the process comprising conversion of a compound of Formula 8c to the compound of Formula 8a.

In illustrative embodiments of the present invention, there is provided a compound of Formula 5a:

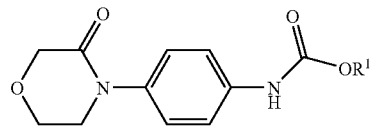
5a wherein
    $R^1$ is alkyl, substituted alkyl, aryl, substituted aryl, arylalkyl, or substituted aryl alkyl.

In illustrative embodiments of the present invention, there is provided a compound of Formula 5a:

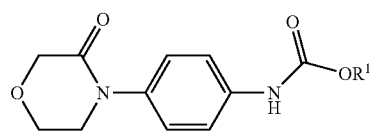
5a wherein
    $R^1$ is alkyl or substituted alkyl.

In illustrative embodiments of the present invention, there is provided a compound of Formula 5b:

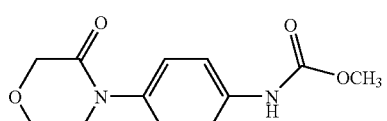
5b

In illustrative embodiments of the present invention, there is provided a compound of Formula 6:

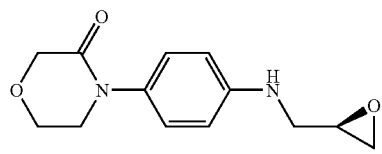
6

In illustrative embodiments of the present invention, there is provided a compound of Formula 8a:

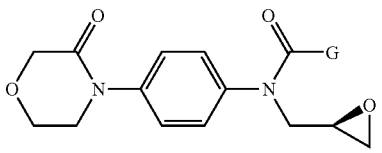
8a wherein
    G is $OR^1$, $NR^2R^3$, or $CX_3$;
    $R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl, $R^2$ and $R^3$, when together form a single ring group with the N to which they are bonded, are a heteroaryl ring; and X is halogen.

In illustrative embodiments of the present invention, there is provided a compound of Formula 8a1:

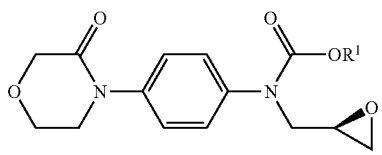

8a1 wherein $R^1$ is alkyl, substituted alkyl, aryl, substituted aryl, arylalkyl, or substituted arylalkyl.

In illustrative embodiments of the present invention, there is provided a compound of Formula 8a1:

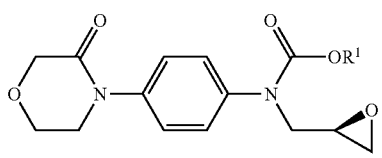

8a1 wherein $R^1$ is alkyl or substituted alkyl.

In illustrative embodiments of the present invention, there is provided a compound of Formula 8a2:

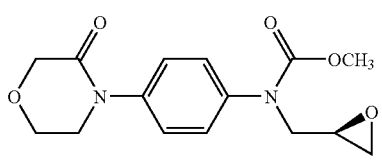

8a2

In illustrative embodiments of the present invention, there is provided a compound of Formula 8c:

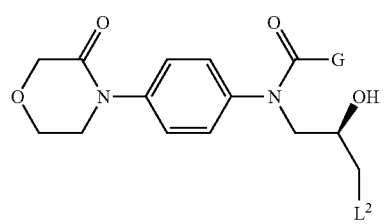

8c wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl, $R^2$ and $R^3$, when together form a single ring group with the N to which they are bonded, are a heteroaryl ring; and $L^2$ is a halogen or sulfonyloxy group.

In illustrative embodiments of the present invention, there is provided a compound of Formula 8c1:

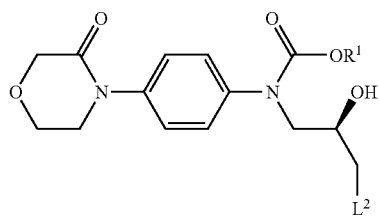

8c1 wherein $R^1$ is alkyl or substituted alkyl and $L^2$ is a halogen or sulfonyloxy group.

In illustrative embodiments of the present invention, there is provided a compound of Formula 8c2:

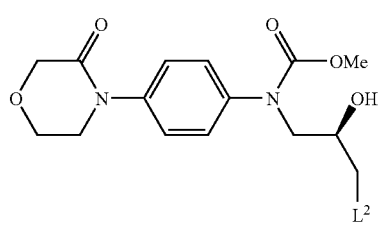

8c2 wherein $L^2$ is a halogen or sulfonyloxy group.

In illustrative embodiments of the present invention, there is provided a compound of Formula 8c3:

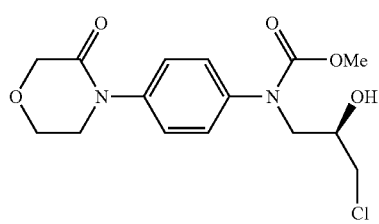

8c3

In illustrative embodiments of the present invention, there is provided a process for the preparation of a compound of Formula 8aa:

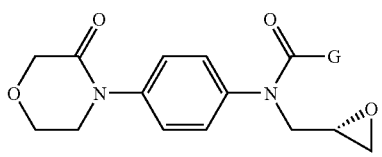

8aa wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl;
$R^2$ and $R^3$ when together form a single ring group with the N to which they are bonded, are a heteroaryl ring; and
X is halogen, the process comprising:
i. reacting, optionally in the presence of a second base, a compound of Formula 2:

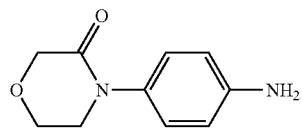

2 with a compound of Formula 3:

3 wherein
$L^1$ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and
G is as defined above for Formula 8aa, thereby forming a compound of Formula 5:

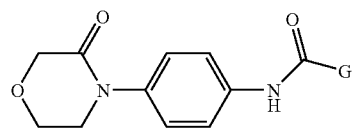

5 wherein G is as defined above for Formula 8aa; and
ii. reacting the compound of Formula 5, in the presence of a third base, with a compound of Formula 4a:

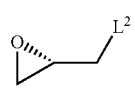

4a wherein $L^2$ is a halogen or sulfonyloxy group, thereby forming the compound of Formula 8aa.

In illustrative embodiments of the present invention, there is provided a process for the preparation of a compound of Formula 8aa:

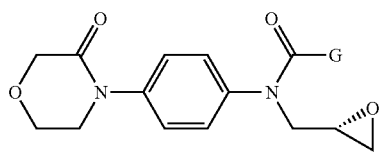

8aa wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl;
$R^2$ and $R^3$ when together form a single ring group with the N to which they are bonded are a heteroaryl ring; and
X is halogen, the process comprising:
i. reacting, in the presence of a fourth base, a compound of Formula 2:

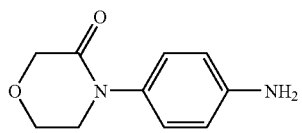

2 with a compound of Formula 4a:

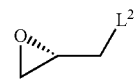

4a wherein $L^2$ is a halogen or sulfonyloxy group, thereby forming a compound of Formula 6a:

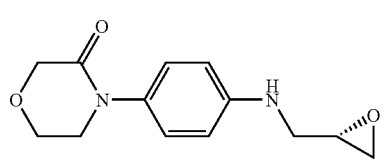

6a and;
ii. reacting, optionally in the presence of a fifth base, the compound of Formula 6a with a compound of Formula 3:

wherein

L¹ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and G is as defined above for Formula 8aa, thereby forming the compound of Formula 8aa.

In illustrative embodiments of the present invention, there is provided a process for the preparation of a compound of Formula 8ca:

*[Structure 8ca]* wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl;

$R^2$ and $R^3$ when together form a single ring group with the N to which they are bonded, are a heteroaryl ring; and $L^2$ is a halogen or sulfonyloxy group, the process comprising:

i. reacting a compound of Formula 2:

*[Structure 2]* with a compound of Formula 4a:

*[Structure 4a]* wherein $L^2$ is a halogen or sulfonyloxy group; thereby forming a compound of Formula 7a:

*[Structure 7a]* wherein $L^2$ is as defined for Formula 4a; and ii. reacting, in the presence of a sixth base, the compound of Formula 7a with a compound of Formula 3:

*[Structure 3]* wherein

L¹ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and G is as defined above for Formula 8ca, thereby forming the compound of Formula 8ca.

In illustrative embodiments of the present invention, there is provided a process for the preparation of a compound of Formula 8aa:

*[Structure 8aa]* wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl;

$R^2$ and $R^3$, when together form a single ring group with the N to which they are bonded, are a heteroaryl ring; X is halogen, the process comprising conversion of a compound of Formula 8ca to the compound of Formula 8aa.

In illustrative embodiments of the present invention, there is provided a compound of Formula 6a:

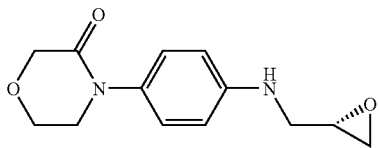

6a

In illustrative embodiments of the present invention, there is provided a compound of Formula 8aa:

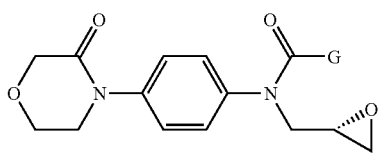

8aa wherein

G is OR$^1$, NR$^2$R$^3$, or CX$_3$;

R$^1$ is alkyl, substituted alkyl, aryl, substituted aryl, arylalkyl, or substituted aryl alkyl;

R$^2$ and R$^3$ are either (a) two independent groups or (b) together form a single ring group with the N to which they are bonded;

R$^2$ and R$^3$, when independent groups, are independently selected from the group consisting of: H, alkyl, substituted alkyl, aryl, substituted aryl, arylalkyl and substituted arylalkyl, R$^2$ and R$^3$, when together form a single ring group with the N to which they are bonded, are a heteroaryl ring; and X is halogen;

In illustrative embodiments of the present invention, there is provided a compound of Formula 8aa1:

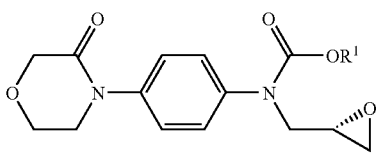

8aa1 wherein

R$^1$ is alkyl, substituted alkyl, aryl, substituted aryl, arylalkyl, or substituted arylalkyl.

In illustrative embodiments of the present invention, there is provided a compound of Formula 8aa1:

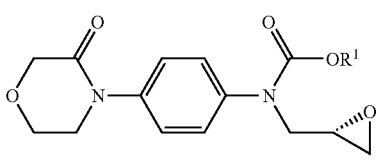

8aa1 wherein

R$^1$ is alkyl or substituted alkyl.

In illustrative embodiments of the present invention, there is provided a compound of Formula 8aa2:

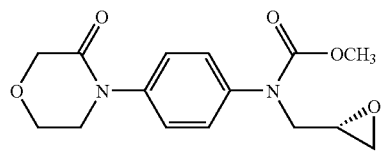

8aa2

In illustrative embodiments of the present invention, there is provided a compound of Formula 8ca:

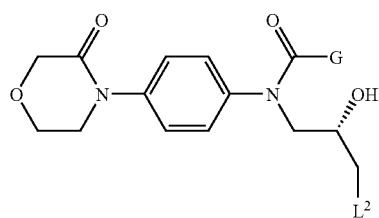

8ca wherein

G is OR$^1$, NR$^2$R$^3$, or CX$_3$;

R$^1$ is alkyl, substituted alkyl, aryl, substituted aryl, arylalkyl, or substituted aryl alkyl;

R$^2$ and R$^3$ are either (a) two independent groups or (b) together form a single ring group with the N to which they are bonded;

R$^2$ and R$^3$, when independent groups, are independently selected from the group consisting of: H, alkyl, substituted alkyl, aryl, substituted aryl, arylalkyl and substituted arylalkyl, R$^2$ and R$^3$, when together form a single ring group with the N to which they are bonded, are a heteroaryl ring; and L$^2$ is a halogen or sulfonyloxy group.

In illustrative embodiments of the present invention, there is provided a compound of Formula 8ca1:

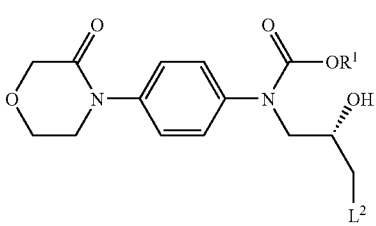

8ca1 wherein

R$^1$ is alkyl or substituted alkyl and L$^2$ is a halogen or sulfonyloxy group.

In illustrative embodiments of the present invention, there is provided a compound of Formula 8ca2:

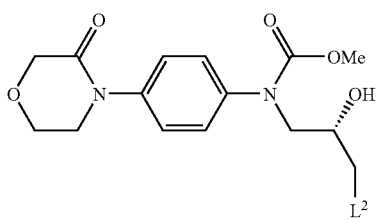

wherein

L² is a halogen or sulfonyloxy group.

In illustrative embodiments of the present invention, there is provided a compound of Formula 8ca3:

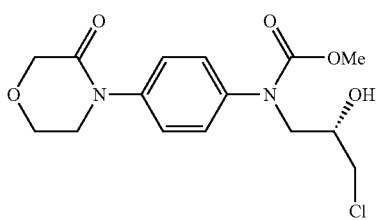

Other aspects and features of the present invention will become apparent to those ordinarily skilled in the art upon review of the following description of specific embodiments of the invention in conjunction with the accompanying figures.

DETAILED DESCRIPTION

As used herein, the term "substituted" refers to the replacement of a hydrogen atom on a compound with a substituent group. A substituent may be a non-hydrogen atom or multiple atoms of which at least one is a non-hydrogen atom and one or more may or may not be hydrogen atoms. For example, without limitation, substituted compounds may comprise one or more substituents selected from the group consisting of: R'', OR'', NR''R''', SR'', halogen, SiR''R'''R'''', OC(O)R'', C(O)R'', CO₂R'', CONR''R''', NR'''C(O)₂R'', S(O)R'', S(O)₂R'', CN, and NO₂.

As used herein, each R'', R''', and R'''' may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

As used herein, the term "alkyl" by itself or as part of another substituent, means, unless otherwise stated, a saturated straight or branched chain, or cyclic hydrocarbon radical, or combination thereof having the number of carbon atoms designated (e.g. $C_1$-$C_{10}$ or 1- to 10-membered means one to ten carbons). When there is no indication of the number of carbon atoms in the alkyl, it is meant, unless otherwise indicated by context, that there are from 1 to 10 carbons. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

As used herein, the term "aryl" by itself or as part of another substituent, means, unless otherwise stated, a polyunsaturated, aromatic, hydrocarbon substituent which can be a single ring or multiple rings (often from 1 to 3 rings) which are fused together or linked covalently. "Aryl" includes, but is not limited to, "heteroaryl" groups. "Heteroaryl" refers to an aryl group that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include: phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl 1,3-furyl 1,2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., aryloxy, arylthioxy, arylalkyl) includes both aryl and heteroaryl rings as defined above. Thus, the term "arylalkyl", is meant to include those radicals in which an aryl group is attached to an alkyl group (e.g., benzyl, phenethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc).

The present invention is directed to methods of preparation of Rivaroxaban, various intermediates useful in the preparation of Rivaroxaban and methods of preparation of such intermediates.

A person of skill in the art recognizes that by appropriate choice of reagents, the processes of the present invention may be equally applied to the preparation of the (R)-enantiomer of Rivaroxaban. By replacing (R)-(−)-epichlorohydrin (compound of Formula 4) of the present invention with (S)-(+)-epichlorohydrin, the (R)-enantiomer of Rivaroxaban is obtained. The processes of the present invention encompass preparation of both enantiomers of Rivaroxaban.

According to illustrative embodiments of the present invention, there is provided a process for the preparation of (S)-Rivaroxaban and/or (R)-Rivaroxaban comprising reacting, in the presence of a first base, a compound of Formula 9:

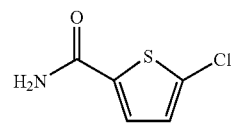

with a compound of Formula 8:

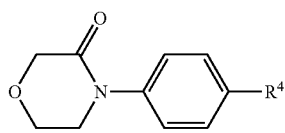

wherein

R⁴ is one of the following:

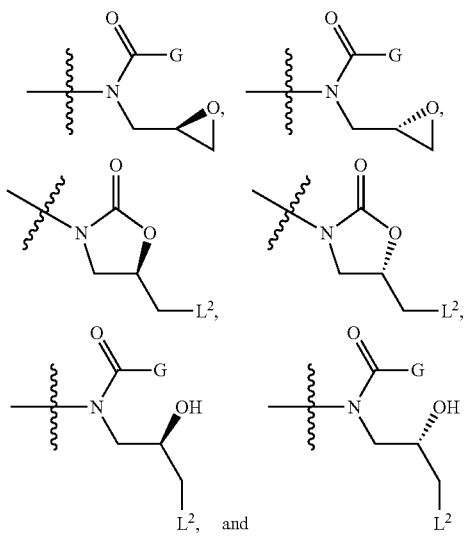

wherein

G is OR¹, NR²R³, or CX₃;

R¹ is alkyl, substituted alkyl, aryl, substituted aryl, arylalkyl, or substituted aryl alkyl;

R² and R³ are either (a) two independent groups or (b) together form a single ring group with the N to which they are bonded;

R² and R³, when independent groups, are independently selected from the group consisting of: H, alkyl, substituted alkyl, aryl, substituted aryl, arylalkyl and substituted arylalkyl, R² and R³, when together form a single ring group with the N to which they are bonded, are a heteroaryl ring;

X is halogen; and

L² is a halogen or sulfonyloxy group.

The first base may be a strong base suitable for deprotonation of an amide. The first base may be an organometallic compound. The organometallic compound may be selected from the group consisting of organomagnesium, organozinc, organosodium, organolithium compounds and mixtures thereof. The first base may be selected from the group consisting of alkylmagnesium halide, arylmagnesium halide, alkylzinc halide, alkyllithium, aryllithium, lithium hexaalkyldisilazide, sodium hexaalkyldisilazide, potassium hexaalkyldisilazide, potassium t-butoxide, sodium hydride, lithium hydride, L-selectride, superhydride, lithium amide, sodium amide, lithium dialkylamide, and mixtures thereof. The first base may be lithium hexamethyldisilazide, n-butyllithium, or potassium t-butoxide. The first base may be combined with an inorganic salt additive such as LiX or CuX wherein X is halogen.

The reaction of the compound of Formula 8 with the compound of Formula 9 may be conducted in a first solvent. The first solvent may be a suitable aprotic organic solvent. The first solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

According to illustrative embodiments of the present invention, there is provided a process for preparation of a compound of Formula 8a:

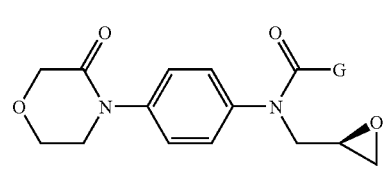

8a wherein

G is OR¹, NR²R³, or CX₃;

R¹ is alkyl, substituted alkyl, aryl, substituted aryl, arylalkyl, or substituted aryl alkyl;

R² and R³ are either (a) two independent groups or (b) together form a single ring group with the N to which they are bonded;

R² and R³, when independent groups, are independently selected from H, alkyl, substituted alkyl, aryl, substituted aryl, arylalkyl and substituted arylalkyl, R² and R³, when together form a single ring group with the N to which they are bonded, are a heteroaryl ring; and X is halogen, the process comprising:

i. reacting, optionally in the presence of a second base, a compound of Formula 2:

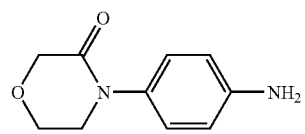

2 with a compound of Formula 3:

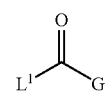

3 wherein

L¹ is a leaving group selected from the group consisting of halogen, imidazole, ester, C₁-C₄ alkoxy, trihalomethoxy, N-hydroxysuccinimide, p-nitrophenol, N-hydroxyphthalimide, and N-hydroxybenzotriazole; and G is as defined above for Formula 8a, thereby forming a compound of Formula 5:

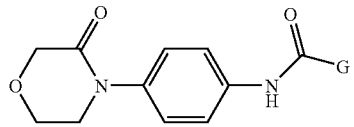

wherein

G is as defined above for Formula 8a; and ii. reacting the compound of Formula 5, in the presence of a third base, with a compound of Formula 4:

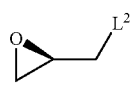

wherein $L^2$ is a halogen or sulfonyloxy group, thereby forming the compound of Formula 8a.

In some embodiments, the compound of Formula 3 is a compound in which $L^1$ is halogen and G is $OR^1$. In some embodiments the compound of Formula 3 is a compound in which $L^1$ is chloro and $R^1$ is alkyl. In some embodiments the compound of Formula 3 is a compound in which $L^1$ is chloro and $R^1$ is methyl. In some embodiments the compound of Formula 3 is a compound in which $L^1$ and G are imidazole.

In some embodiments the compound of Formula 4 is a compound in which $L^2$ is a sulfonyloxy group. In some embodiments the compound of Formula 4 is a compound in which $L^2$ is a toluenesulfonyloxy, methanesulfonyloxy or trifluoromethanesulfonyloxy group. In some embodiments the compound of Formula 4 is a compound in which $L^2$ is a halogen. In some embodiments the compound of Formula 4 is a compound in which $L^2$ is chloro.

The second base may be inorganic or organic. The second base may be selected from the group consisting of metal hydroxides, carbonates, phosphates, tertiary amines, and aryl amines. The second base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

The reaction of the compound of Formula 2 with the compound of Formula 3 may be conducted in a second solvent. The second solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and suit ones (e.g. dimethyl sulfoxide and sulfolane), halogenated hydrocarbons (e.g. dichloromethane and dichloroethane), alcohols (e.g. methanol, ethanol, isopropanol, butanol), water and mixtures thereof.

The third base may be a suitable non-nucleophilic base. The third base may be selected from the group consisting of lithium hexamethyldisilazide, lithium dialkyl amide, sodium hydride, potassium t-butoxide and n-butyllithium.

The reaction of the compound of Formula 5 with the compound of Formula 4 may be conducted in a third solvent. The third solvent may be a suitable aprotic organic solvent. The third solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

According to illustrative embodiments of the present invention, there is provided a process for the preparation of a compound of Formula 8a:

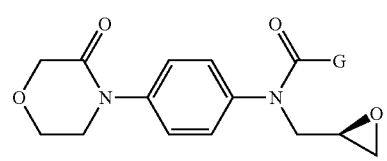

wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl, $R^2$ and $R^3$, when together form a single ring group with the N to which they are bonded, are a heteroaryl ring; and X is halogen, the process comprising:

i. reacting, in the presence of a fourth base, a compound of Formula 2:

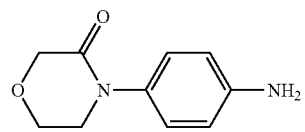

with a compound of Formula 4:

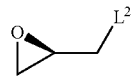

wherein
L² is a halogen or sulfonyloxy group, thereby forming a compound of Formula 6:

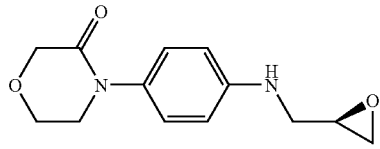

and;
ii. reacting, optionally in the presence of a fifth base, the compound of Formula 6 with a compound of Formula 3:

wherein
L¹ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and G is as defined above for Formula 8a, thereby forming the compound of Formula 8a.

In some embodiments the compound of Formula 4 is a compound in which L² is a sulfonyloxy group. In some embodiments the compound of Formula 4 is a compound in which L² is a toluenesulfonyloxy, methanesulfonyloxy or trifluoromethanesulfonyloxy group. In some embodiments the compound of Formula 4 is a compound in which L² is a halogen. In some embodiments the compound of Formula 4 is a compound in which L² is chloro.

In some embodiments the compound of Formula 3 is a compound in which L¹ is halogen and G is OR¹. In some embodiments the compound of Formula 3 is a compound in which L¹ is chloro and R¹ is alkyl. In some embodiments the compound of Formula 3 is a compound in which L¹ is chloro and R¹ is methyl. In some embodiments the compound of Formula 3 is a compound in which L¹ and G are imidazole.

The fourth base may be inorganic or organic. The fourth base may be selected from the group consisting of metal hydroxides, carbonates, phosphates, tertiary amines, and aryl amines. The fourth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

Reaction of the compound of Formula 2 with the compound of Formula 4 may be conducted in a fourth solvent. The fourth solvent may be selected from the group consisting of alkyl ethers (e.g. tetrahydrofuran, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), alcohols (e.g. methanol, ethanol, isopropanol, butanol), water and mixtures thereof.

The fifth base may be inorganic or organic. The fifth base may be selected from the group consisting of metal hydroxides, carbonates, phosphates, tertiary amines, and aryl amines. The fifth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

In some embodiments, the compound of Formula 2 may be treated with the compound of Formula 4 without base to yield an intermediate of Formula 7, which may or may not be isolated, before treatment with a fourth base to yield the compound of Formula 6.

Reaction of the compound of Formula 6 with the compound of Formula 3 may be conducted in a fifth solvent. The fifth solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), alcohols (e.g. methanol, ethanol, isopropanol, butanol), water and mixtures thereof.

According to illustrative embodiments of the present invention, there is provided a process for preparation of a compound of Formula 8c:

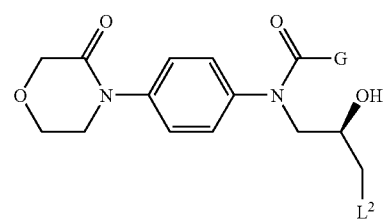

wherein
G is OR¹, NR²R³, or CX₃;

R¹ is alkyl, substituted alkyl, aryl, substituted aryl, arylalkyl, or substituted aryl alkyl;

R² and R³ are either (a) two independent groups or (b) together form a single ring group with the N to which they are bonded;

R² and R³, when independent groups, are independently selected from the group consisting of: H, alkyl, substituted alkyl, aryl, substituted aryl, arylalkyl and substituted arylalkyl, R² and R³, when together form a single ring group with the N to which they are bonded, are a heteroaryl ring; and L² is a halogen or sulfonyloxy group, the process comprising:

i. reacting a compound of Formula 2:

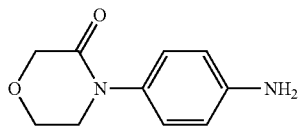

with a compound of Formula 4:

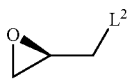

wherein
$L^2$ is a halogen or sulfonyloxy group; thereby forming a compound of Formula 7:

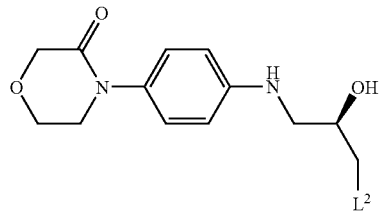

wherein
$L^2$ is as defined for Formula 4,
and;
ii. reacting, in the presence of a sixth base, the compound of Formula 7 with a compound of Formula 3:

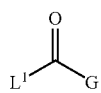

wherein
$L^1$ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and
G is as defined above for Formula 8c, thereby forming the compound of Formula 8c.

In some embodiments the compound of Formula 4 is a compound in which $L^2$ is a sulfonyloxy group. In some embodiments the compound of Formula 4 is a compound in which $L^2$ is a toluenesulfonyloxy, methanesulfonyloxy or trifluoromethanesulfonyloxy group. In some embodiments the compound of Formula 4 is a compound in which $L^2$ is a halogen. In some embodiments the compound of Formula 4 is a compound in which $L^2$ is chloro.

In some embodiments the compound of Formula 3 is a compound in which $R^1$ is alkyl. In some embodiments the compound of Formula 3 is a compound in which $R^1$ is methyl. In some embodiments the compound of Formula 3 is a compound in which X is chloro and $R^1$ is methyl.

The sixth base may be inorganic or organic. The sixth base may be selected from the group consisting of metal hydroxides, carbonates, phosphates, tertiary amines and aryl amines. The sixth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

Reaction of the compound of Formula 2 with the compound of Formula 4 may be conducted in a sixth solvent that is the same as the fourth solvent above.

Reaction of the compound of Formula 7 with the compound of Formula 3 may be conducted in a seventh solvent that is the same as the fifth solvent above.

According to illustrative embodiments of the present invention, there is provided a process for the preparation of a compound of Formula 8a:

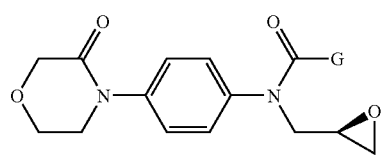

wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl,
$R^2$ and $R^3$, when together form a single ring group with the N to which they are bonded, are a heteroaryl ring; and
X is halogen,
the process comprising conversion of a compound of Formula 8c to the compound of Formula 8a.

Conversion of the compound of Formula 8c to the compound of Formula 8a may be conducted by treatment of the compound of Formula 8c with a suitable alkali halide optionally in the presence of a seventh base. The suitable alkali halide may be sodium iodide. The seventh base may be the same as the sixth base above.

A compound of Formula 8b:

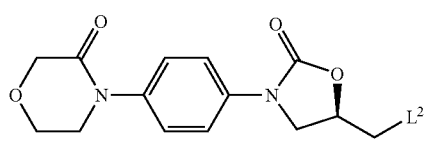

wherein
$L^2$ is as defined above for Formula 4, may be prepared from the compound of Formula 7 or the compound of Formula 8c. For example, when the compound of Formula 7 is treated with the compound of Formula 3 in the presence of a suitable base, the cyclized compound of Formula 8b may be obtained. Similarly, the compound of Formula 8c may be converted to the compound of Formula 8b under suitable conditions. For example, when the compound of Formula 8c is treated with a suitable base, the compound of Formula 8b may be obtained.

Other methods for converting the compound of Formula 7 or Formula 8c to the compound of Formula 8b are known to those skilled in the art.

According to illustrative embodiments of the present invention, there is provided a process for preparation of a compound of Formula 8aa:

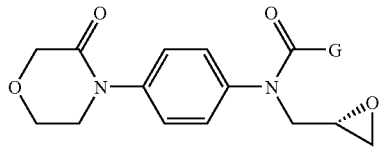

wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups, are independently selected from H, alkyl, substituted alkyl, aryl, substituted aryl, arylalkyl and substituted arylalkyl, $R^2$ and $R^3$, when together form a single ring group with the N to which they are bonded, are a heteroaryl ring; and X is halogen, the process comprising:

i. reacting, optionally in the presence of a second base, a compound of Formula 2:

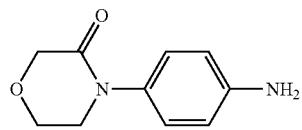

with a compound of Formula 3:

wherein $L^1$ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and G is as defined above for Formula 8aa, thereby forming a compound of Formula 5:

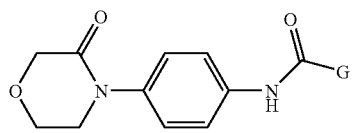

wherein

G is as defined above for Formula 8aa; and ii. reacting the compound of Formula 5, in the presence of a third base, with a compound of Formula 4a:

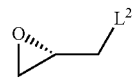

wherein $L^2$ is a halogen or sulfonyloxy group, thereby forming the compound of Formula 8aa.

In some embodiments, the compound of Formula 3 is a compound in which $L^1$ is halogen and G is $OR^1$. In some embodiments the compound of Formula 3 is a compound in which $L^1$ is chloro and $R^1$ is alkyl. In some embodiments the compound of Formula 3 is a compound in which $L^1$ is chloro and $R^1$ is methyl. In some embodiments the compound of Formula 3 is a compound in which $L^1$ and G are imidazole.

In some embodiments the compound of Formula 4a is a compound in which $L^2$ is a sulfonyloxy group. In some embodiments the compound of Formula 4a is a compound in which $L^2$ is a toluenesulfonyloxy, methanesulfonyloxy or trifluoromethanesulfonyloxy group. In some embodiments the compound of Formula 4a is a compound in which $L^2$ is a halogen. In some embodiments the compound of Formula 4a is a compound in which $L^2$ is chloro.

The second base may be inorganic or organic. The second base may be selected from the group consisting of metal hydroxides, carbonates, phosphates, tertiary amines, and aryl amines. The second base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

The reaction of the compound of Formula 2 with the compound of Formula 3 may be conducted in a second solvent. The second solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), alcohols (e.g. methanol, ethanol, isopropanol, butanol), water and mixtures thereof.

The third base may be a suitable non-nucleophilic base. The third base may be selected from the group consisting of lithium hexamethyldisilazide, lithium dialkyl amide, sodium hydride, potassium t-butoxide and n-butyllithium.

The reaction of the compound of Formula 5 with the compound of Formula 4a may be conducted in a third solvent. The third solvent may be a suitable aprotic organic solvent. The third solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone, aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof. According to illustrative embodiments of the present invention, there is provided a process for the preparation of a compound of Formula 8aa:

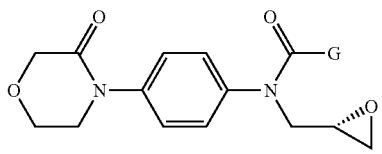

8aa wherein
G is $OR^1$, $NR^2R^3$, or $CX_3$;
$R^1$ is alkyl, substituted alkyl, aryl, substituted aryl, arylalkyl, or substituted aryl alkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl,
$R^2$ and $R^3$, when together form a single ring group with the N to which they are bonded, are a heteroaryl ring; and
X is halogen,
the process comprising:
i. reacting, in the presence of a fourth base, a compound of Formula 2:

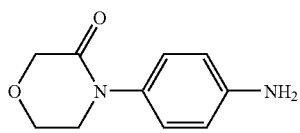

2 with a compound of Formula 4a:

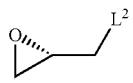

4a wherein
$L^2$ is a halogen or sulfonyloxy group, thereby forming a compound of Formula 6a:

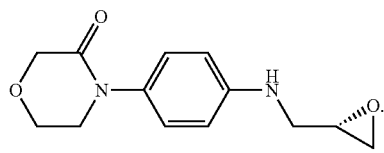

6a and;
ii. reacting, optionally in the presence of a fifth base, the compound of Formula 6a with a compound of Formula 3:

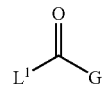

3 wherein
$L^1$ is a leaving group selected from the group consisting of halogen, imidazole, ester, $C_1$-$C_4$ alkoxy, trihalomethoxy, N-hydroxysuccinimide, p-nitrophenol, N-hydroxyphthalimide, and N-hydroxybenzotriazole; and
G is as defined above for Formula 8a, thereby forming the compound of Formula 8aa.

In some embodiments the compound of Formula 4a is a compound in which $L^2$ is a sulfonyloxy group. In some embodiments the compound of Formula 4a is a compound in which $L^2$ is a toluenesulfonyloxy, methanesulfonyloxy or trifluoromethanesulfonyloxy group. In some embodiments the compound of Formula 4a is a compound in which $L^2$ is a halogen. In some embodiments the compound of Formula 4a is a compound in which $L^2$ is chloro.

In some embodiments the compound of Formula 3 is a compound in which $L^1$ is halogen and G is $OR^1$. In some embodiments the compound of Formula 3 is a compound in which $L^1$ is chloro and $R^1$ is alkyl. In some embodiments the compound of Formula 3 is a compound in which $L^1$ is chloro and $R^1$ is methyl. In some embodiments the compound of Formula 3 is a compound in which $L^1$ and G are imidazole.

The fourth base may be inorganic or organic. The fourth base may be selected from the group consisting of metal hydroxides, carbonates, phosphates, tertiary amines, and aryl amines. The fourth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

Reaction of the compound of Formula 2 with the compound of Formula 4a may be conducted in a fourth solvent. The fourth solvent may be selected from the group consisting of alkyl ethers (e.g. tetrahydrofuran, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), alcohols (e.g. methanol, ethanol, isopropanol, butanol), water and mixtures thereof.

The fifth base may be inorganic or organic. The fifth base may be selected from the group consisting of metal hydroxides, carbonates, phosphates, tertiary amines, and aryl amines. The fifth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

In some embodiments, the compound of Formula 2 may be treated with the compound of Formula 4a without base to yield an intermediate of Formula 7a, which may or may not be isolated, before treatment with a fourth base to yield the compound of Formula 6a.

Reaction of the compound of Formula 6a with the compound of Formula 3 may be conducted in a fifth solvent. The fifth solvent may be selected from the group consisting of alkyl ethers (e.g. tetrahydrofuran, dioxane, diethyl ether, methyl t-butyl ether, diisopropyl ether, butyl ether), alkyl esters (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and suit ones (e.g. dimethyl sulfoxide and sulfolane), halogenated hydrocarbons (e.g. dichloromethane and dichloroethane), alcohols (e.g. methanol, ethanol, isopropanol, butanol), and mixtures thereof.

According to illustrative embodiments of the present invention, there is provided a process for preparation of a compound of Formula 8ca:

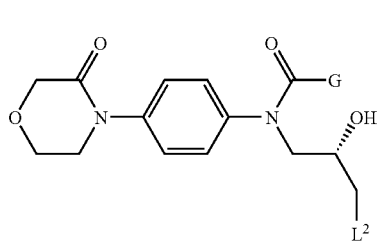

wherein

G is OR$^1$, NR$^2$R$^3$, or CX$_3$;

R$^1$ is alkyl, substituted alkyl, aryl, substituted aryl, arylalkyl, or substituted aryl alkyl;

R$^2$ and R$^3$ are either (a) two independent groups or (b) together form a single ring group with the N to which they are bonded;

R$^2$ and R$^3$, when independent groups, are independently selected from the group consisting of: H, alkyl, substituted alkyl, aryl, substituted aryl, arylalkyl and substituted arylalkyl, R$^2$ and R$^3$, when together form a single ring group with the N to which they are bonded, are a heteroaryl ring; and L$^2$ is a halogen or sulfonyloxy group, the process comprising:

i. reacting a compound of Formula 2:

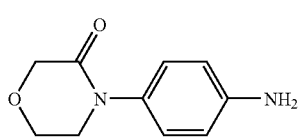

with a compound of Formula 4a:

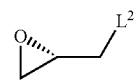

wherein

L$^2$ is a halogen or sulfonyloxy group; thereby forming a compound of Formula 7a:

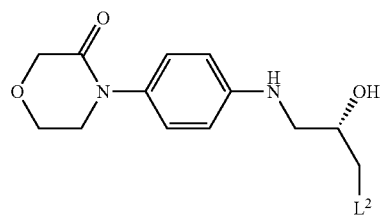

wherein

L$^2$ is as defined for Formula 4, and;

ii. reacting, in the presence of a sixth base, the compound of Formula 7a with a compound of Formula 3:

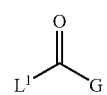

wherein

L$^1$ is a leaving group selected from the group consisting of halogen, imidazole, ester, C$_1$-C$_4$ alkoxy, trihalomethoxy, N-hydroxysuccinimide, p-nitrophenol, N-hydroxyphthalimide, and N-hydroxybenzotriazole; and G is as defined above for Formula 8ca, thereby forming the compound of Formula 8ca.

In some embodiments the compound of Formula 4a is a compound in which L$^2$ is a sulfonyloxy group. In some embodiments the compound of Formula 4a is a compound in which L$^2$ is a toluenesulfonyloxy, methanesulfonyloxy or trifluoromethanesulfonyloxy group. In some embodiments the compound of Formula 4a is a compound in which L$^2$ is a halogen. In some embodiments the compound of Formula 4a is a compound in which L$^2$ is chloro.

In some embodiments the compound of Formula 3 is a compound in which R$^1$ is alkyl. In some embodiments the compound of Formula 3 is a compound in which R$^1$ is methyl. In some embodiments the compound of Formula 3 is a compound in which X is chloro and R$^1$ is methyl.

The sixth base may be inorganic or organic. The sixth base may be selected from the group consisting of metal hydroxides, carbonates, phosphates, tertiary amines and aryl amines. The sixth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylethylamine, N,N-dimethylaniline, N,N-diethylaniline, pyridine, and mixtures thereof.

Reaction of the compound of Formula 2 with the compound of Formula 4a may be conducted in a sixth solvent that is the same as the fourth solvent above.

Reaction of the compound of Formula 7a with the compound of Formula 3 may be conducted in a seventh solvent that is the same as the fifth solvent above.

According to illustrative embodiments of the present invention, there is provided a process for the preparation of a compound of Formula 8aa:

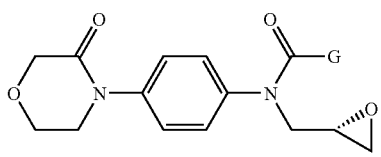

8aa wherein

G is $OR^1$, $NR^2R^3$, or $CX_3$;

$R^1$ is alkyl, substituted alkyl, aryl, substituted aryl, arylalkyl, or substituted aryl alkyl;

$R^2$ and $R^3$ are either (a) two independent groups or (b) together form a single ring group with the N to which they are bonded;

$R^2$ and $R^3$, when independent groups; are independently selected from the group consisting of: H, alkyl, substituted alkyl, aryl, substituted aryl, arylalkyl and substituted arylalkyl, $R^2$ and $R^3$, when together form a single ring group with the N to which they are bonded, are a heteroaryl ring; and X is halogen, the process comprising conversion of a compound of Formula 8ca to the compound of Formula 8aa.

Conversion of the compound of Formula 8ca to the compound of Formula 8aa may be conducted by treatment of the compound of Formula 8ca with a suitable alkali halide optionally in the presence of a seventh base. The suitable alkali halide may be sodium iodide. The seventh base may be the same as the sixth base above.

A compound of Formula 8ba:

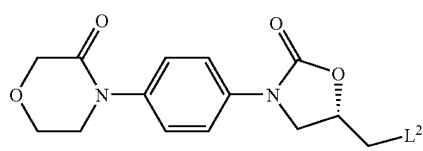

8ba wherein $L^2$ is as defined above for Formula 4a, may be prepared from the compound of Formula 7a or the compound of Formula 8ca. For example, when the compound of Formula 7a is treated with the compound of Formula 3 in the presence of a suitable base, the cyclized compound of Formula 8ba may be obtained. Similarly, the compound of Formula 8ca may be converted to the compound of Formula 8ba under suitable conditions. For example, when the compound of Formula 8ca is treated with a suitable base, the compound of Formula 8ba may be obtained. Other methods for converting the compound of Formula 7a or Formula 8ca to the compound of Formula 8ba are known to those skilled in the art.

EXAMPLES

The following examples are illustrative of some of the embodiments of the invention described herein. These examples should not be considered to limit the spirit or scope of the invention in any way.

Example 1

Preparation of methyl N-[4-(3-oxo-4-morpholinyl)phenyl]carbamate (5b): N,N-Diisopropylethylamine (27.2 mL, 156.08 mmol) was added over 3 min to a stirred suspension of 4-(4-aminophenyl)-3-morpholinone (2, 25 g, 130.07 mmol) in $CH_2Cl_2$ (750 mL). The reaction mixture was stirred at room temperature for 15 min and methyl chloroformate (11.6 mL, 149.58 mmol) was added drop-wise over 10 min. The resulting thick suspension was stirred for another 1 h and filtered through a Buchner funnel. The solid was washed with $CH_2Cl_2$ (2×75 mL) and dried under vacuum to obtain methyl N-[4-(3-oxo-4-morpholinyl)phenyl]carbamate (5b, 30.92 g, 95%) as a crystalline solid.

$^1$HNMR (300 MHz, DMSO-d6) δ 3.66-3.69 (m, 2H), 3.67 (s, 3H), 3.93-3.97 (m, 2H), 4.17 (s, 2H), 7.28 (d, J=8.8 Hz, 2H), 7.46 (d, J=8.8 Hz, 2H), 9.72 (brs, 1H).

Example 2

Preparation of Methyl N-(2R,3-epoxy-1-propyl)-N-[4-(3-oxo-4-morpholinyl)phenyl]carbamate (8a2): NaH (1.772 g, 48 mmol, 65% in mineral oil) was washed with heptane (30 mL) under a nitrogen atmosphere and DMF (30 mL) was added. A suspension of methyl N-[4-(3-oxo-4-morpholinyl)phenyl]carbamate (5b, 10 g, 40 mmol) in DMF (60 mL) was added in one portion. (R)-(–)-epichlorohydrin (4.7 mL, 60, mmol) was added and the reaction mixture was heated at 60° C. for 3 h. The reaction mixture was cooled to room temperature and diluted with a mixture of water (700 mL) and sat. aq. $NH_4Cl$. The aqueous layer was extracted with EtOAc (100 mL) followed by $CH_2Cl_2$ (3×100 mL). The combined organic layers were dried ($Na_2SO_4$) and evaporated. The residue was purified by flash chromatography over silica gel (6×20 cm) using 70% EtOAc-heptane to obtain methyl N-(2R,3-epoxy-1-propyl)-N-[4-(3-oxo-4-morpholinyl)phenyl]carbamate (8a2, 5.075 g, 42%) as a crystalline solid.

$^1$HNMR (400 MHz, $CDCl_3$) δ 2.55 (dd, J=5.5, 2.5 Hz, 1H), 2.82 (t, J=4.5 Hz, 1H), 3.24-3.28 (m, 1H), 3.54, (dd, J=14.8, 6.1 Hz, 1H), 3.72 (s, 3H), 3.77 (m, 2H), 3.98 (dd, J=14.8, 3.8 Hz, 1H), 4.03 (m, 2H), 4.33 (s, 2H), 7.34 (s, 4H).

Example 3

Preparation of 4-[4-(N-(2R,3-epoxy-1-propyl)amino)phenyl]morpholin-3-one (6): R-(–)epichlorohydrin (1.3 mL, 16.5 mmol) was added to a suspension of 4-(4-aminophenyl)-3-morpholinone (2, 2.883 g, 15 mmol) in IPA (75 mL). The reaction mixture was refluxed for 20 h and a solution of $NaHCO_3$ (1.513 g, 18 mmol) in water (30 mL) was added and reflux continued for another 1.5 h. Solvent was evaporated using a rotary evaporator and the residue was diluted with water (100 mL) and extracted with EtOAc (3×50 mL). Combined organic extracts were dried ($Na_2SO_4$), evaporated and the residue was purified by flash chromatography over silica gel (4×12 cm) using 80% EtOAc-heptane to obtain 4-[4-(N-(2R,3-epoxy-1-propyl)amino)phenyl]morpholin-3-one (6, 1.675 g, 46%) as a crystalline white solid.

$^1$HNMR (300 MHz, $CDCl_3$) δ 2.69 (dd, J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.96-4.02 (m, 3H), 4.32 (s, 2H), 6.66 (d, J=8.7 Hz, 2H), 7.11 (d, J=8.7 Hz, 2H).

Example 4

Preparation of Methyl N-(2R,3-epoxy-1-propyl)-N-[4-(3-oxo-4-morpholinyl)phenyl]carbamate (8a2): Methyl chloroformate (0.17 mL, 2.214 mmol) and N,N-Diisopropylethylamine (0.39 mL, 2.214 mmol) were added in that order to a stirred and cooled (0° C.) solution of 4-[4-(N-(2R,3-epoxy-1-propyl)amino)phenyl]morpholin-3-one (6, 500 mg, 2.013 mmol) in MeCN (10 mL). The cooling bath was removed after 5 min and stirring continued for another 30 min. The reaction mixture was diluted with water (70 mL) and extracted with EtOAc (3×30 mL). The combined organic extracts were dried ($Na_2SO_4$), evaporated and the residue was purified by flash chromatography over silica gel (2×16 cm) using 90% EtOAc-heptane to obtain methyl N-(2R,3-epoxy-1-propyl)-N-[4-(3-oxo-4-morpholinyl)phenyl]carbamate (8a2, 536 mg, 87%) as a crystalline white solid.

$^1$HNMR (400 MHz, $CDCl_3$) δ 2.55 (dd, J=5.5, 2.5 Hz, 1H), 2.82 (t, J=4.5 Hz, 1H), 3.24-3.28 (m, 1H), 3.54, (dd, J=14.8, 6.1 Hz, 1H), 3.72 (s, 3H), 3.77 (m, 2H), 3.98 (dd, J=14.8, 3.8 Hz, 1H), 4.03 (m, 2H), 4.33 (s, 2H), 7.34 (s, 4H).

Example 5

Preparation of 4-[4-(N-(3-chloro-2R-hydroxy-1-propyl)amino)phenyl]morpholin-3-one (7, $L^2$ is chloro): R(−)-epichlorohydrin (2.12 mL, 27.053 mmol) was added to a refluxing solution of 4-(4-aminophenyl)-3-morpholinone (2, 4.0 g, 20.81 mmol) in IPA (125 mL). The mixture was refluxed for 24 h and the solvent was evaporated in vacuo. The residue was purified by flash chromatography over silica gel (4×22 cm) using 90% EtOAc-hexane to obtain 4-[4-(N-(3-chloro-2R-hydroxy-1-propyl)amino)phenyl]morpholin-3-one (7, $L^2$ is chloro, 4.89 g, 83%) as a crystalline white solid. Alternatively the crude residue can be purified by crystallization in EtOAc-hexane (2:1).

1HNMR (300 MHz, CDCl3) d 2.80 (d, J=5.1 Hz, 1H), 3.15-3.22 (m, 1H), 3.33-3.38 (m, 1H), 3.57-3.71 (m, 4H), 3.96-4.05 (m, 3H), 4.13 (br s, 1H), 4.17 (s, 2H), 6.60-6.65 (m, 2H), 7.07-7.11 (m, 2H).

Example 6

Preparation of methyl N-(3-chloro-2R-hydroxy-1-propyl)-N-[4-(3-oxo-4-morpholinyl)phenyl]carbamate (8c3): Methyl chloroformate (0.05 mL, 0.631 mmol) and N,N-diisopropylethylamine (0.09 mL, 0.5 mmol) were, added in that order to a stirred solution of 4-[4-(N-(3-chloro-2R-hydroxy-1-propyl)amino)phenyl]morpholin-3-one (7, $L^2$ is chloro, 150 mg, 0.526 mmol) in MeCN (5 mL). The mixture was stirred at room temperature for 1 h and solvent was evaporated in vacuo at 30-35° C. The residue was taken up in $CH_2Cl_2$ (25 mL) and washed with water (10 mL). The organic layer was dried ($Na_2SO_4$), evaporated and dried under vacuum to obtain methyl N-(3-chloro-2R-hydroxy-1-propyl)-N-[4-(3-oxo-4-morpholinyl)phenyl]carbamate (8c3, 181 mg, ca. 100%).

1 HNMR (300 MHz, $CDCl_3$) d 3.45 (br s, 1H), 3.52 (dd, J=11.2, 5.5 Hz, 1H), 3.60 (dd, J=11.2, 5.0 Hz, 1H), 3.67-3.80 (m, 3H), 3.70 (s, 3H), 3.88-3.96 (m, 1H), 4.02-4.06 (m, 3H), 4.34 (s, 2H), 7.28-7.37 (m, 4H).

Example 7

Preparation of Rivaroxaban: n-BuLi (2.36 mL, 3.77 mmol, 1.6 M in hexane) was added drop-wise (over ca. 2-3 min) to a stirred and cooled (−10° C.) suspension of 5-chlorothiophene-2-carboxamide (9, 831 mg, 5.141 mmol) in THF (8 mL). The cooling bath was removed after 30 min and the reaction mixture was stirred for another 30 min. Methyl N-(2R,3-epoxy-1-propyl)-N-[4-(3-oxo-4-morpholinyl)phenyl]carbamate (8a2, 1.05 g, 3.427 mmol) was added as a solid in one portion. The reaction mixture was then refluxed for 5 h and the solvent evaporated in vacuo. A mixture of cold water (30 mL; ~5° C.) and saturated aqueous $NH_4Cl$ (10 mL) was added to the damp residue. The mixture was stirred for 10 min, filtered and washed the solids with cold (~5° C.) water (2×10 mL). The solid was pulped in MeOH (40 mL) at 60° C. for 1 h, concentrated to ~10 mL and cooled to room temperature. The solids were filtered, washed with cold (0° C.) MeOH (2×4 mL) and dried under vacuum to obtain Rivaroxaban (925 mg, 62%) as a crystalline solid.

Example 8

Preparation of Rivaroxaban: LiCl (17 mg, 0.391 mmol) was added to a solution of t-BuOK (42 mg, 0.359 mmol) in THF (1 mL). After stirring for 30 min, 5-chlorothiophene-2-carboxamide (9, 79 mg, 0.489 mmol) was added. The suspension was stirred for another 30 min and methyl N-(2R,3-epoxy-1-propyl)-N-[4-(3-oxo-4-morpholinyl)phenyl]carbamate (8a2, 100 mg, 0.326 mmol) was added. The reaction mixture was refluxed for 4 h and the solvent was evaporated using a rotary evaporator. A mixture of cold water (8 mL; ~5° C.) and saturated aqueous $NH_4Cl$ (2 mL) was added to the damp residue. The mixture was stirred for 10 min, filtered and washed the solids with cold (~5° C.) water (2×2 mL). The solid was dissolved in MeOH (8 mL) and concentrated using a rotary evaporator to ~1 mL. The precipitated solids were filtered, washed with cold (0° C.) MeOH (0.5 mL) and dried under vacuum to obtain Rivaroxaban (44 mg, 31%) as a crystalline solid.

Example 9

Preparation of Rivaroxaban: LiHMDS (0.36 mL, 0.36 mmol, 1M in THF) was added dropwise to a suspension of 5-chlorothiophene-2-carboxamide (9, 95 mg, 0.587 mmol) in THF (1 mL). The resulting homogeneous solution was stirred at room temperature for 15 min and methyl N-(2R,3-epoxy-1-propyl)-N-[4-(3-oxo-4-morpholinyl)phenyl]carbamate (8a2, 100 mg, 0.326 mmol) was added as a solid. The reaction mixture was refluxed for 3 h during which time solids separated out. The solvent was evaporated in vacuo and a mixture of cold (5° C.) water (8 mL) plus sat. aq. $NH_4Cl$ (2 mL) was added to the damp solids. The solids were filtered and washed with cold (5° C.) water (5 ml). The solids were dissolved in 1:1 mixture of MeOH—$CH_2Cl_2$ (10 mL) and concentrated on a rotary evaporator, to ~1 mL. The precipitated solids were filtered, washed with cold (5° C.) MeOH (2×0.5 mL) and dried under vacuum to obtain Rivaroxaban (90 mg, 64%) as a crystalline solid.

$^1$HNMR (300 MHz, $CDCl_3$) δ 3.59-3.62 (m, 2H), 3.69-3.73 (m, 2H), 3.85 (dd, J=8.9, 6.3 Hz, 1H), 3.95-3.99 (m, 2H), 4.16-4.22 (m, 1H), 4.19 (s, 2H), 4.82-4.86 (m, 1H), 7.19 (d, J=4.2 Hz, 1H), 7.40 (d, J=8.7 Hz, 2H), 7.56 (d, J=8.7 Hz, 2H), 7.69 (d, J=4.2 Hz, 1H), 8.97 (t, J=5.5 Hz, 1H).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range: The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

The invention claimed is:

1. A compound of Formula 5a:

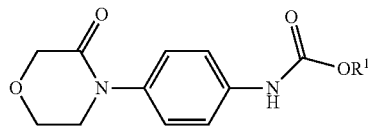

wherein
 $R^1$ is alkyl, substituted alkyl, aryl, substituted aryl, arylalkyl, or substituted aryl alkyl, provided that the substituted aryl is not substituted with $NO_2$.

2. The compound of claim 1 wherein $R^1$ is alkyl or substituted alkyl.

3. A compound of Formula 5b:

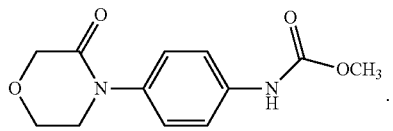

4. A compound of Formula 6:

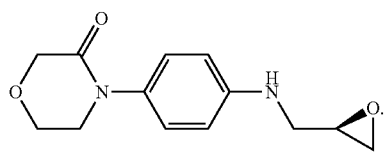

5. A compound of Formula 8a:

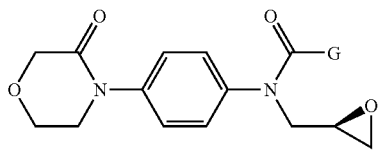

wherein
 G is $OR^1$, $NR^2R^3$, or $CX_3$;
 $R^1$ is alkyl, substituted alkyl, aryl, substituted aryl, arylalkyl, or substituted aryl alkyl;
 $R^2$ and $R^3$ are either (a) two independent groups or (b) together form a single ring group with the N to which they are bonded;
 $R^2$ and $R^3$, when independent groups, are independently selected from the group consisting of: H, alkyl, substituted alkyl, aryl, substituted aryl, arylalkyl and substituted arylalkyl,
 $R^2$ and $R^3$, when together form a single ring group with the N to which they are bonded, are a heteroaryl ring; and
 X is halogen.

6. A compound of Formula 8a1:

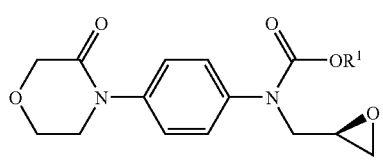

wherein
 $R^1$ is alkyl, substituted alkyl, aryl, substituted aryl, arylalkyl, or substituted arylalkyl.

7. The compound of claim 6 wherein $R^1$ is alkyl or substituted alkyl.

8. A compound of Formula 8a2:

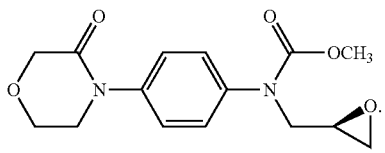

9. A compound of Formula 8c:

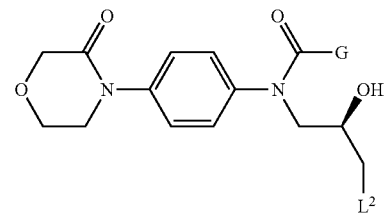

wherein
 G is $OR^1$, $NR^2R^3$, or $CX_3$;
 $R^1$ is alkyl, substituted alkyl, aryl, substituted aryl, arylalkyl, or substituted aryl alkyl;
 $R^2$ and $R^3$ are either (a) two independent groups or (b) together form a single ring group with the N to which they are bonded;
 $R^2$ and $R^3$, when independent groups, are independently selected from the group consisting of: H, alkyl, substituted alkyl, aryl, substituted aryl, arylalkyl and substituted arylalkyl, R² and R³, when together form a single ring group with the N to which they are bonded, are a heteroaryl ring; and L² is a halogen or sulfonyloxy group.

10. A compound of Formula 8c1:

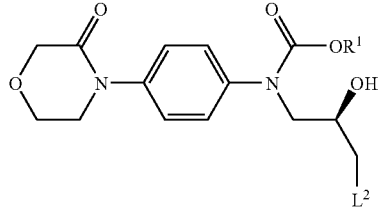

wherein

R¹ is alkyl or substituted alkyl and L² is a halogen or sulfonyloxy group.

11. A compound of Formula 8c2:

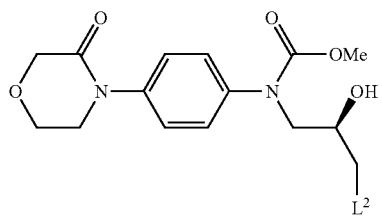

wherein

L² is a halogen or sulfonyloxy group.

12. A compound of Formula 8c3:

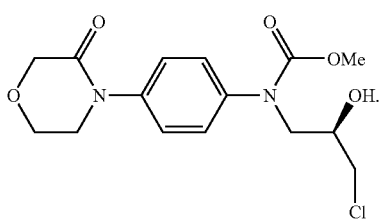

13. A compound of Formula 6a:

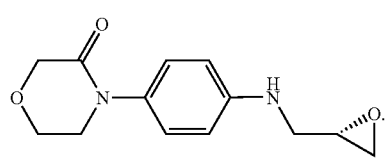

14. A compound of Formula 8aa:

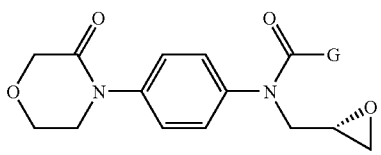

wherein

G is $OR^1$, $NR^2R^3$, or $CX_3$;

R¹ is alkyl, substituted alkyl, aryl, substituted aryl, arylalkyl, or substituted aryl alkyl;

R² and R³ are either (a) two independent groups or (b) together form a single ring group with the N to which they are bonded;

R² and R³, when independent groups, are independently selected from the group consisting of: H, alkyl, substituted alkyl, aryl, substituted aryl, arylalkyl and substituted arylalkyl, R² and R³, when together form a single ring group with the N to which they are bonded, are a heteroaryl ring; and X is halogen.

15. A compound of Formula 8aa1:

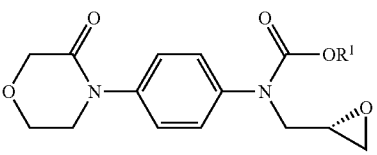

wherein

R¹ is alkyl, substituted alkyl, aryl, substituted aryl, arylalkyl, or substituted arylalkyl.

16. The compound of claim 15 wherein R¹ is alkyl or substituted alkyl.

17. A compound of Formula 8aa2:

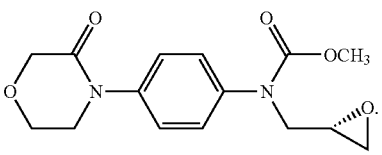

18. A compound of Formula 8ca:

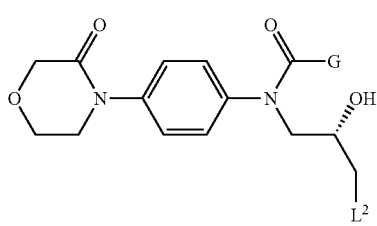

wherein
G is OR$^1$, NR$^2$R$^3$, or CX$_3$;
R$^1$ is alkyl, substituted alkyl, aryl, substituted aryl, arylalkyl, or substituted aryl alkyl;
R$^2$ and R$^3$ are either (a) two independent groups or (b) together form a single ring group with the N to which they are bonded;
R$^2$ and R$^3$, when independent groups, are independently selected from the group consisting of: H, alkyl, substituted alkyl, aryl, substituted aryl, arylalkyl and substituted arylalkyl,
R$^2$ and R$^3$, when together form a single ring group with the N to which they are bonded, are a heteroaryl ring; and
L$^2$ is a halogen or sulfonyloxy group.

19. A compound of Formula 8ca1:

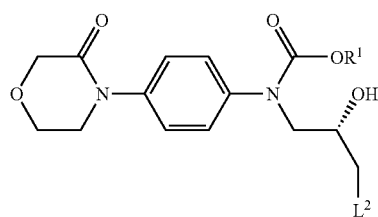

wherein
R$^1$ is alkyl or substituted alkyl; and
L$^2$ is a halogen or sulfonyloxy group.

20. A compound of Formula 8ca2:

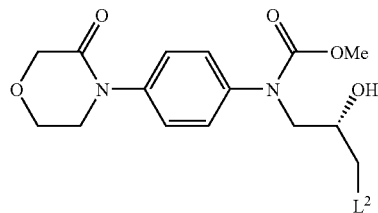

wherein
L$^2$ is a halogen or sulfonyloxy group.

21. A compound of Formula 8ca3:

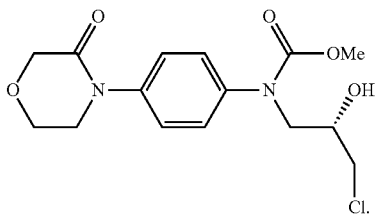

22. A composition comprising S-Rivaroxaban and at least one of compounds 8a, 8b and 8c:

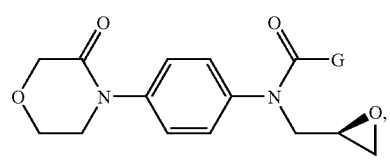

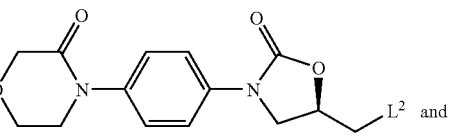

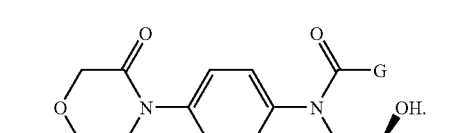

* * * * *